(12) United States Patent
Drost

(10) Patent No.: US 8,968,204 B2
(45) Date of Patent: Mar. 3, 2015

(54) SYSTEM AND METHOD OF PERIVASCULAR PRESSURE AND FLOW MEASUREMENT

(75) Inventor: Cornelis J. Drost, Ithaca, NY (US)

(73) Assignee: Transonic Systems, Inc., Ithaca, NY (US)

( * ) Notice: Subject to any disclaimer, the term of this patent is extended or adjusted under 35 U.S.C. 154(b) by 2160 days.

(21) Appl. No.: 11/818,209

(22) Filed: Jun. 12, 2007

(65) Prior Publication Data
US 2008/0021325 A1 Jan. 24, 2008

Related U.S. Application Data

(60) Provisional application No. 60/812,845, filed on Jun. 12, 2006.

(51) Int. Cl.
*A61B 8/00* (2006.01)
*A61B 5/021* (2006.01)
*A61B 8/06* (2006.01)

(52) U.S. Cl.
CPC .. *A61B 8/06* (2013.01); *A61B 5/021* (2013.01)
USPC ........... 600/454; 600/459; 600/485; 600/500; 600/561

(58) Field of Classification Search
None
See application file for complete search history.

(56) References Cited

U.S. PATENT DOCUMENTS

| | | | | |
|---|---|---|---|---|
| 3,987,673 | A * | 10/1976 | Hansen | 73/861.25 |
| 4,198,987 | A * | 4/1980 | Cain et al. | 600/457 |
| 4,227,407 | A * | 10/1980 | Drost | 73/861.28 |
| 4,336,808 | A * | 6/1982 | Ohno et al. | 600/459 |
| 4,476,874 | A * | 10/1984 | Taenzer et al. | 600/441 |
| 4,926,875 | A * | 5/1990 | Rabinovitz et al. | 600/504 |
| 4,987,900 | A | 1/1991 | Eckerle et al. | |
| 5,165,416 | A | 11/1992 | Shinoda et al. | |
| 5,284,150 | A * | 2/1994 | Butterfield et al. | 600/485 |
| 5,423,323 | A * | 6/1995 | Orth | 600/486 |
| 5,797,879 | A * | 8/1998 | DeCampli | 604/93.01 |
| 5,807,258 | A * | 9/1998 | Cimochowski et al. | 600/454 |
| 5,830,131 | A * | 11/1998 | Caro et al. | 600/300 |
| 5,967,986 | A * | 10/1999 | Cimochowski et al. | 600/454 |
| 5,967,989 | A * | 10/1999 | Cimochowski et al. | 600/459 |
| 6,231,516 | B1 * | 5/2001 | Keilman et al. | 600/485 |
| 6,237,398 | B1 * | 5/2001 | Porat et al. | 73/54.09 |
| 6,277,078 | B1 * | 8/2001 | Porat et al. | 600/486 |
| 6,398,734 | B1 * | 6/2002 | Cimochowski et al. | 600/454 |
| 6,475,170 | B1 * | 11/2002 | Doron et al. | 600/587 |
| 6,486,588 | B2 * | 11/2002 | Doron et al. | 310/322 |
| 6,522,926 | B1 * | 2/2003 | Kieval et al. | 607/44 |
| 6,554,774 | B1 * | 4/2003 | Miele | 600/485 |
| 6,585,763 | B1 * | 7/2003 | Keilman et al. | 623/1.42 |
| 6,595,071 | B1 * | 7/2003 | Doten | 73/861.29 |
| 6,659,949 | B1 * | 12/2003 | Lang et al. | 600/438 |

(Continued)

OTHER PUBLICATIONS

Ziaie et al: An Implantable Blood Pressure Sensor Cuff for Tonometric Blood Pressure Measurement (2 pages).

(Continued)

*Primary Examiner* — Long V Le
*Assistant Examiner* — Nicholas Evoy
(74) *Attorney, Agent, or Firm* — Brian B. Shaw, Esq.; Harter Secrest & Emery LLP

(57) ABSTRACT

A system and method for measuring fluid flow and pressure in a flexible conduit is disclosed. An embodiment of the system and method uses an ultrasound sensor for determining volume of flow and a tonometric system for determining pressure along a common length of a flexible conduit.

26 Claims, 6 Drawing Sheets

(56) References Cited

U.S. PATENT DOCUMENTS

| | | | |
|---|---|---|---|
| 6,704,185 B2 | 3/2004 | Chatzandroulis et al. | |
| 6,730,038 B2* | 5/2004 | Gallant et al. | 600/485 |
| 6,850,801 B2* | 2/2005 | Kieval et al. | 607/44 |
| 6,868,739 B1* | 3/2005 | Krivitski et al. | 73/861.05 |
| 6,985,774 B2* | 1/2006 | Kieval et al. | 607/44 |
| 6,986,744 B1* | 1/2006 | Krivitski | 600/504 |
| 7,087,034 B2* | 8/2006 | McPherson et al. | 604/8 |
| 7,158,832 B2* | 1/2007 | Kieval et al. | 607/44 |
| 7,427,265 B1* | 9/2008 | Keilman et al. | 600/300 |
| 7,500,403 B2* | 3/2009 | Konzelmann et al. | 73/861.29 |
| 7,559,894 B2* | 7/2009 | McEowen | 600/438 |
| 7,616,997 B2* | 11/2009 | Kieval et al. | 607/44 |
| 7,617,001 B2* | 11/2009 | Penner et al. | 607/60 |
| 7,647,831 B2* | 1/2010 | Corcoran et al. | 73/700 |
| 7,813,812 B2* | 10/2010 | Kieval et al. | 607/118 |
| 7,840,271 B2* | 11/2010 | Kieval et al. | 607/44 |
| 7,857,767 B2* | 12/2010 | Ferren et al. | 600/481 |
| 7,892,191 B2* | 2/2011 | Zumeris et al. | 601/46 |
| 7,949,400 B2* | 5/2011 | Kieval et al. | 607/44 |
| 7,966,886 B2* | 6/2011 | Corcoran et al. | 73/700 |
| 7,998,060 B2* | 8/2011 | Ferren et al. | 600/114 |
| 8,060,206 B2* | 11/2011 | Kieval et al. | 607/44 |
| 8,086,314 B1* | 12/2011 | Kieval | 607/44 |
| 8,137,276 B2* | 3/2012 | Petruzzello et al. | 600/439 |
| 8,290,595 B2* | 10/2012 | Kieval et al. | 607/44 |
| 8,353,896 B2* | 1/2013 | Hillis et al. | 604/890.1 |
| 8,560,076 B2* | 10/2013 | Kieval et al. | 607/46 |
| 8,666,472 B2* | 3/2014 | Maltz et al. | 600/407 |
| 8,694,092 B2* | 4/2014 | Ferren et al. | 607/2 |
| 8,718,789 B2* | 5/2014 | Bolea et al. | 607/117 |
| 2004/0254469 A1* | 12/2004 | Shkarlet et al. | 600/459 |
| 2005/0038346 A1* | 2/2005 | Miele | 600/485 |
| 2005/0070799 A1* | 3/2005 | Vilkomerson et al. | 600/454 |
| 2005/0126268 A1* | 6/2005 | Ouriev et al. | 73/54.41 |
| 2009/0270695 A1* | 10/2009 | McEowen | 600/301 |
| 2011/0196237 A1* | 8/2011 | Pelissier et al. | 600/454 |
| 2012/0203113 A1* | 8/2012 | Skerl et al. | 600/473 |

OTHER PUBLICATIONS

Quick et al: Resolving the Hemodynamic Inverse Problem (8 pages) IEEE Transactions on Biomedical Engineering, vol. 53, No. 3, Mar. 2006.

Kosaka et al: Online Parameter Identification of Second-Order Systemic Circulation Model Using the Delta Operator (8 pages) Blackwell Publishing, Inc. p. 967-970 (2002).

Mukkamala et al: Continuous Cardiac Output Monitoring by Peripheral Blood Pressure Waveform Analysis (9 pages) IEEE Transactions on Biomedical Engineering, vol. 53, No. 3, Mar. 2006.

Drzewiecki et al: Arterial Tonometry: Review and Analysis (12 pages) J. Biomechanics vol. 16, No. 2, pp. 141-152 (1983).

Chen et al: Estimation of Central Aortic Pressure Waveform by Mathematical Transformation of Radial Tonometry Pressure (28 pages)—http://circ.ahajournals.org/cgi/content/full/95/7/1827 (Feb. 25, 2005).

Ziaie et al: An Implantable Pressure Sensor Cuff for Tonometric Blood Pressure Measurement (4 pages).

* cited by examiner

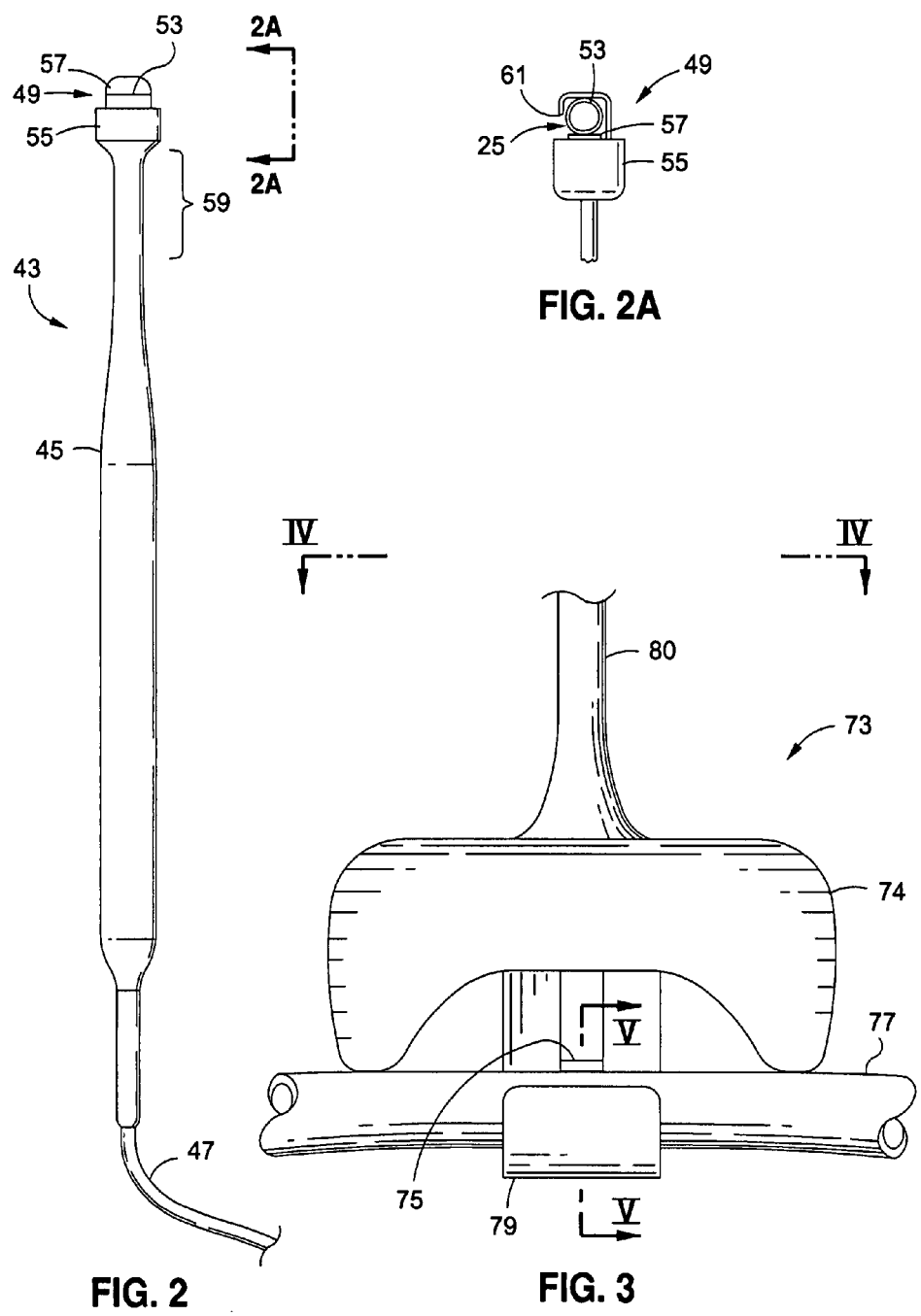

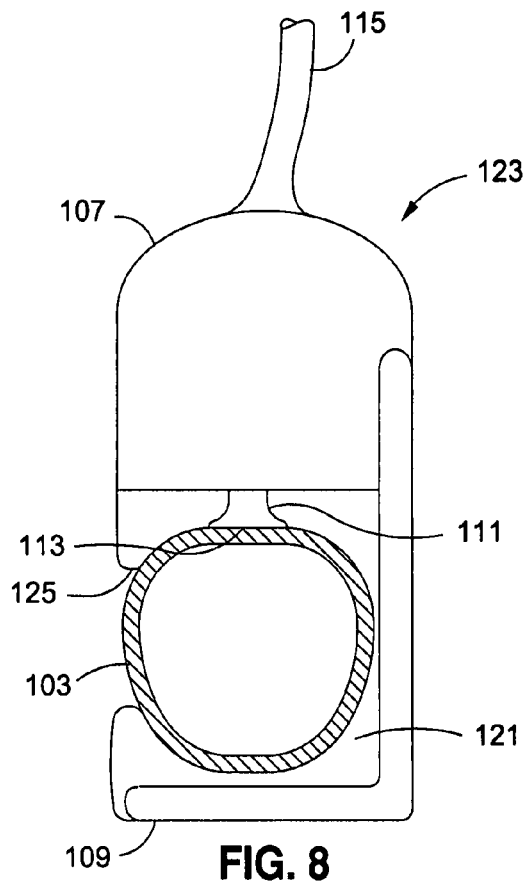
FIG. 8
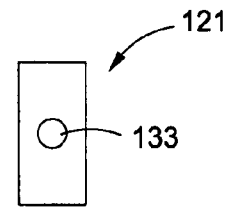
FIG. 10
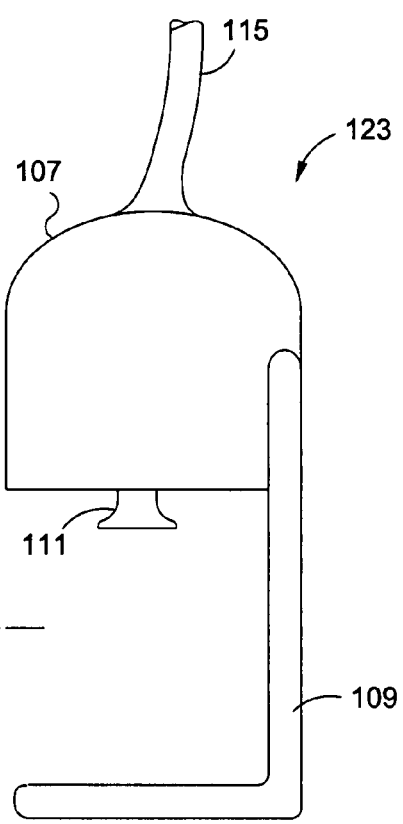
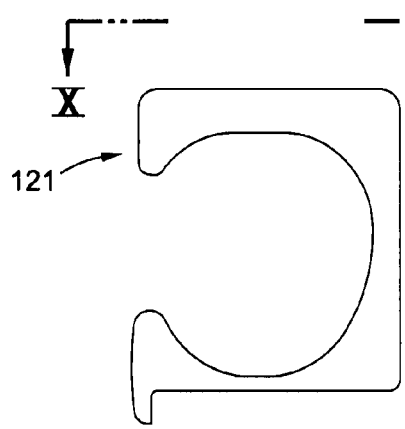
FIG. 9

SYSTEM AND METHOD OF PERIVASCULAR PRESSURE AND FLOW MEASUREMENT

CROSS-REFERENCE TO RELATED APPLICATIONS

The present application claims priority under 35 USC §119 (e) from U.S. provisional application Ser. No. 60/812,845 filed Jun. 12, 2006 with the title of "System and Method of Perivascular Pressure and Flow Measurement".

STATEMENT REGARDING FEDERALLY SPONSORED RESEARCH OR DEVELOPMENT

Not applicable.

REFERENCE TO A "SEQUENCE LISTING"

Not applicable.

BACKGROUND OF THE INVENTION

1. Field of the Invention

The present invention relates to a system and method for measuring, a pressure and flow of blood, more particularly it is related to the perivascular measurement of blood flow and pressure at the same location on a blood vessel.

2. Background of the Invention

Blood flow and blood pressure measurement provide useful physiological information in biological systems. If flow and pressure are measured at the same location of a blood vessel, the measurement can allow a determination of the impedance of the tissue or organs to which the vessel is supplying blood.

At present localized pressure measurement in a blood vessel is commonly made with a sensor placed at the end of a catheter tip which is inserted into the blood stream. Because of the invasive nature of the catheter, and the possible change in flow and pressure that can result from introducing a foreign object into the blood stream, use of a catheter has limitations. Also chronic or long term measurements can not be made with a catheter since prolonged insertion of the catheter into the blood vessel causes the patient's immune system to treat the catheter as a foreign body and tissue will form around the catheter thus degrading the ability of the catheter to measure flow and pressure.

Another pressure measurement principle is the tonometric approach, where a pressure sensor is pressed against the outside of a vessel. If certain conditions are met, the pressure sensed in this manner will be equal to the blood pressure inside the vessel. Although the tonometric principle of blood pressure measurement is known and has found use for the non-invasive measurement of intra-arterial pressure (see for instance U.S. Pat. No. 5,284,150) tonometrics has not been adopted as an implantable method for measuring the localized blood pressure of a vessel due to a number of technical problems. A discussion of the general theory behind the technique appears in the article "Arterial Tonometry: Review and Analysis" by Drzewiecki, Melbin and Noordergraaf in the J. Biomechanics Vol. 16 No. 2 pp, 141-152 (1983).

Perivascular measurement of blood volume flow with ultrasound has been a standard technique which has been used since the 1980's. U.S. Pat. No. 4,227,407, describes a perivascular system and method of ultrasound measurement. The principles described in this patent have been applied in the development of transit time flow sensors by Transonic Systems Inc. of Ithaca, N.Y. Doppler flow velocity measurements have been documented since the 1970's, and may be used as an alternate flow measurement approach.

Thus, what is needed is a system and method to obtain in real time pressure and flow readings in a blood vessel or other type of flexible conduit. There is also a need for a system and method to obtain continuous readings of flow and pressure in a blood vessel or other type of flexible conduit over an extended period of time without loss of accuracy in the readings.

SUMMARY

Thus, it is an objective of the present invention to provide a system and method of obtaining at the same location on a blood vessel or other flexible conduit in real time volume flow and pressure measurements. It is a further objective to obtain such readings using a single perivascular sensor without penetration of the vessel or conduit wall. It is yet still a further objective to be able to make these readings in real time over an extended period of time.

The present disclosure achieves these and other objectives by providing: a method for determining fluid flow and pressure of a fluid flowing in a flexible conduit having the steps of: a) making a volume flow or flow velocity measurement using an ultrasound wave beam passed into a conduit at an oblique angle to the a fluid flowing in the conduit; b) flattening a portion of the conduit; and c) obtaining a pressure reading at some or all of the flattened portion of the flexible conduit.

Yet another aspect of the disclosure provides a system for measuring flow volume and pressure in a flexible conduit having: a) a first ultrasound transducer and a second ultrasound transducer detachably positioned adjacent to said location of the flexible conduit, the first transducer being positioned upstream of the second transducer to transmit ultrasound beams between the transducers that illuminate and pass through a full cross sectional area of the conduit; b) a meter operatively connected to the first transducer and the second transducer to control operation of and receive signals from the transducers representative of the characteristics of the ultrasound beam before and after transmission of the ultrasound beam through the conduit to thereby calculate volume flow; c) a pressure transducer detachably positioned on the same location of the conduit against an outside surface of the conduit such that the pressure transducer shapes the adjacent surface of the flexible conduit into a flat surface, and d) operatively connecting to the meter to control operation of and to receive signals from the pressure transducer, which signals are representative of a pressure inside the conduit.

BRIEF DESCRIPTION OF THE DRAWINGS

The invention will be better understood by an examination of the following description, together with the accompanying drawings, in which:

FIG. 2 is a full raised view of one embodiment of flow pressure sensor perivascular probe;

FIG. 2A is a side view of a probe head of FIG. 2 along line 2A with a conduit inserted into the probe head;

FIG. 3 is a front view of another variation of a flow-pressure sensor perivascular probe;

FIG. 8 provides a cross sectional review of another variation of an implantable probe;

FIG. 9 is an exploded view of the probe and cuff of FIG. 8;

FIG. 10 is a view of the top of the cuff of FIGS. 8 and 9;

DETAILED DESCRIPTION OF THE PREFERRED EMBODIMENT

Figure 1:
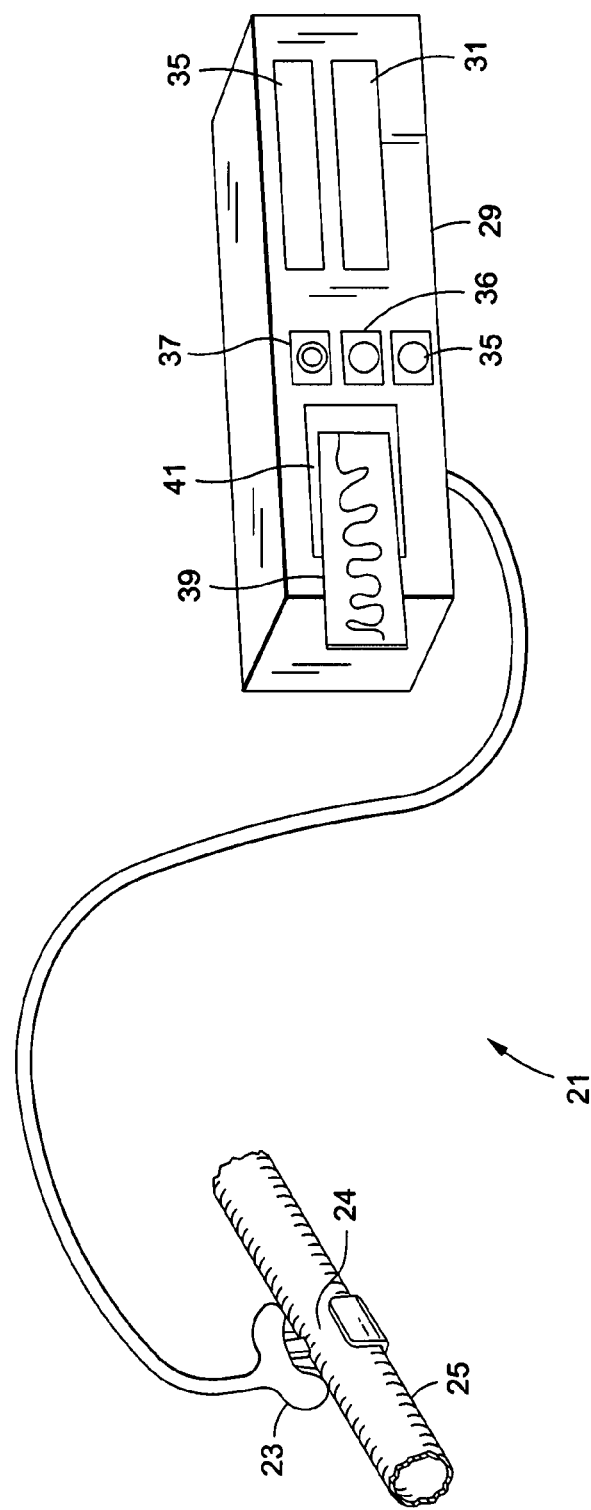
FIG. 1 is a schematic diagram of a perivascular system for measuring flow and pressure.

FIG. 1 is a schematic diagram of the major functional components of the present flow and pressure measurement system 21. System 21 includes a probe 23 that measures both blood flow and pressure at a common location on a blood vessel 25 to which probe 23 has been attached. Probe 23 attaches by an electrical lead 27 to a combined flow and pressure meter 29. Probe 23 includes ultrasound transducers 81A and 81B to measure flow and a tonometric pressure measurement sensor which will be described in detail below.

The present system can use a perivascular ultrasound system similar to the one described in U.S. Pat. No. 4,227,407, which is expressly incorporated herein by reference as if set out herein, and discloses the basic features of this type of perivascular ultrasound measurement system.

Meter 29 is a standard Transonic HT314 surgical meter made by Transonic Systems Inc. that has the added capability of measuring blood pressure as well as blood flow. Screen 31 can display mean volume of flow, flow messages or signal quality information as directed by knob 33. Screen 35 displays pressure, pressure massages or information on signal quality as directed by knob 36. Knob 37 controls the graph printing device 41. Knob 37 directs the printer to print pressure, flow or a combination of both on graph printing paper 39.

FIG. 2 provides a raised view of one variation of a flow and pressure sensor probe 43. Probe 43 has a handle 45 that has an electrical lead 47 that passes through the handle and connects with a probe head 49. Probe head 49 includes a combination clip and ultrasound reflector 53 which attaches to a housing 55, which includes both ultrasound transducers 81A and 81B (not shown in FIG. 2) and a tonometric pressure sensor. Probe 43 has a flexible neck 59 to allow for the positioning of probe head 49 such as around a vessel in a patient. FIG. 2A provides a side view of probe head 49. The inner surface 61 of clip 53 acts as a reflective surface for the ultrasound transducers 81A and 81B located in housing 55. The interior of housing 55 will be discussed in more detail. As shown in FIG. 2A clip 53 holds a vessel 25 securely but detachably against housing 55.

As noted above, the probe 43 also measures blood pressure of blood flowing in a vessel with a tonometric blood pressure sensing device. FIG. 3 is a close up view of the front of a probe head 73. A housing 74 contains ultrasonic transducers (not shown in FIG. 3) and a tonometric pressure sensor 75 that projects out of housing 74 and abuts against conduit or blood vessel 77. Clip 79 also projects out of housing 74 to securely hold conduit or blood vessel 77 against housing 74. Electrical lead 80 carries electrical signals between the ultrasonic transducers (not shown in FIG. 3) and the tonometric pressure sensor 75 and the flow and pressure meter 29.

Figure 4:
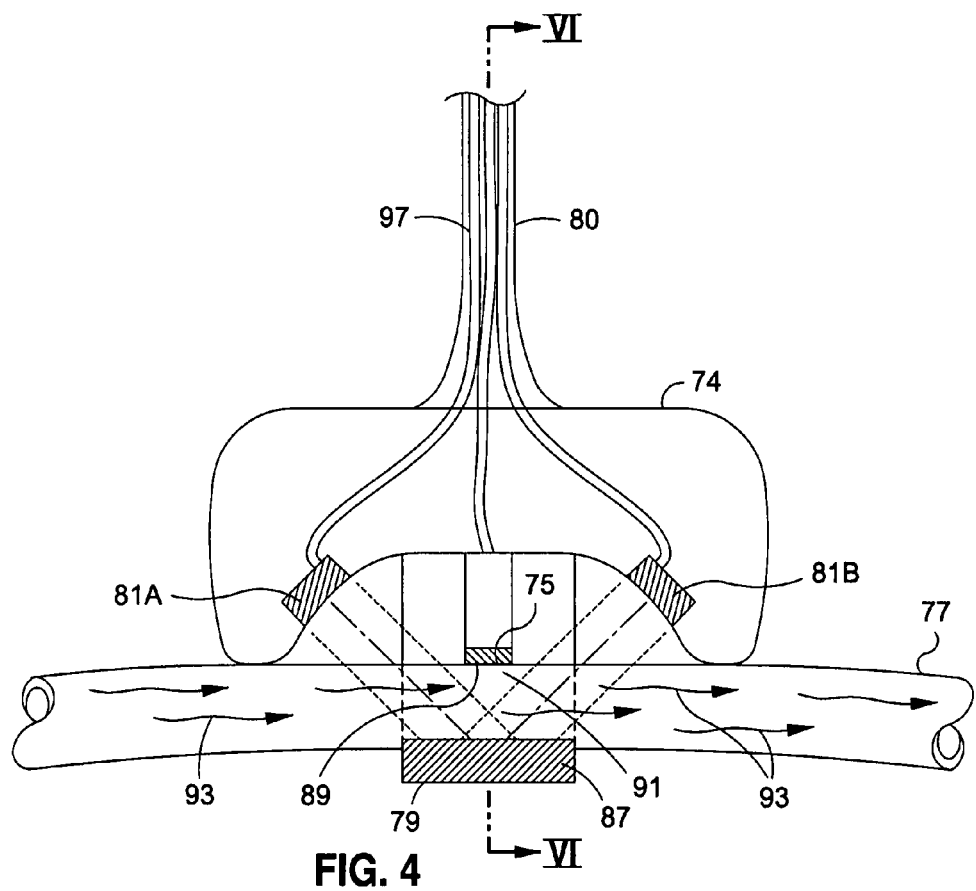
FIG. 4 is a cut away cross sectional view of the probe in FIG. 3 along line IV-IV.

FIG. 4 is a cut away cross-sectional view of probe head 73 and vessel 77 along line IV-IV in FIG. 3. FIG. 4 shows the position of ultrasound transducers 81A and 81B that are located inside housing 74. Ultrasound transducers 81A and 81B are positioned to exchange ultrasound transmissions that are reflected off of an interior surface 87 of clip 79. Readings of flow volume of the blood in vessel 77 are taken from the ultrasound transmissions produced by the transducers and analyzed as indicated above. Tonometric pressure sensor 75 has a flat sensing surface 89 that shapes the portion of vessel 77 that the surface abuts against into a flat surface to obtain the necessary readings. Blood flow in the cut away view of vessel 77 is indicated by arrows 93.

Figure 5:
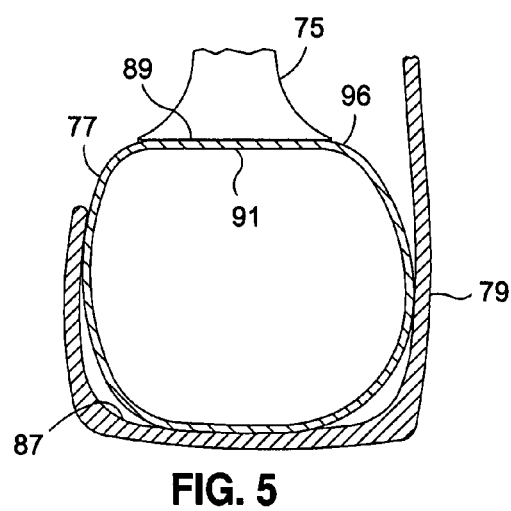
FIG. 5 is a detailed cut away cross sectional view of a portion of the probe of FIG. 3 along line V-V.

FIG. 5 is a detailed cut away view of vessel 77, tonometric sensor 75 and clip 79 along lines V-V of FIG. 3. In FIG. 5 the flat surface 91 shape of the vessel wall 96 by the flat sensing surface 89 of tonometric sensor 75 can be seen. In order to make the pressure measurements with a tonometric sensor 75, the sensing surface of the tonometric sensor must always conform or shape the adjacent portion of the blood vessel into a flat surface. Tonometric sensing of pressure is based on the principle that when a portion of the surface of a flexible conduit is flattened, the pressure outside and inside the vessel at the flattened portion of the blood vessel will be equal. Thus, a sensor taking a pressure reading at the flattened portion of the surface of the blood vessel will be reading the pressure in the adjacent interior portion of the blood vessel. This concept is based on Laplaces's law for a pressure gradient across a vessel's wall which is expressed in the following equation:

$$Pout - Pin = \frac{T}{r} \qquad [1]$$

In this equation Pout is the pressure outside the wall of the vessel and Pin is the pressure on the inside of vessel. T is the vessel wall tension and r is the radius of the vessel. Equation 1 can be modified as follows by simple algebraic manipulation:

$$Pout = \frac{T}{r} + Pin \qquad [2]$$

If the wall of the vessel is then flattened in effect then the radius r goes to infinity r=∞. Thus substituting this value for r in the above equation results in T/r going to zero so the above equation can be reduced to the following:

$$Pout=Pin \qquad [3]$$

Thus as can be seen the pressure differential across the vessel wall at the flattened portion goes to zero ΔP→0.

The tonometric sensing surface 89 is flat to thereby conform or dispose the adjacent vessel wall into a flat and rigid surface necessary for the pressure measurement. Various types of semiconductor sensing elements could be embedded in the flat surface 89 to make the pressure measurements at the flattened surface 91. These could be capacitive type of pressure sensors, strain gauges, etc. These devices are typically made of piezoelectrical active types of materials that are naturally sensitive to the application of mechanical stress. As can be seen in FIG. 4, electrical connections 97 run from the ultrasonic transducers 81A and 81B as well as tonometric sensor 85 up through electrical line conduit 80 to the flow-pressure meter 29 (not shown).

Figure 6:
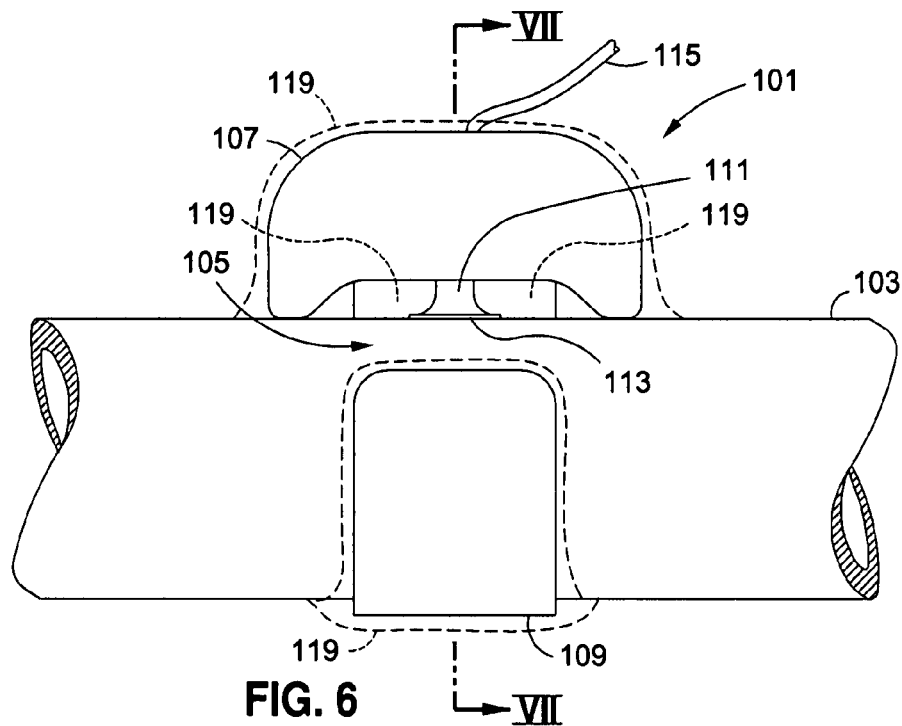
FIG. 6 is a front view of an implantable probe.

FIG. 6 provides an enlarged view of another variation of a flow-pressure sensor probe 101. The variation of the disclosure in FIG. 6 would be implanted into a test subject such as a laboratory rat, sheep, horse etc. for chronic, long term measurements. The probe 101 would naturally be placed around a blood vessel 103 by inserting the blood vessel through a gap 105 formed by housing 107 and clip 109. Since vessel 103 is flexible and easily deformable the vessel 103 may be inserted through gap 105. Probe 101 is sized such that a sensing surface 113 of a tonometric sensor 111 abuts firmly up against an outside wall of vessel 103 and forms the flat surface described previously that allows for the direct tonometric measurement of pressure. Alternatively, an insert sized to fit into the probe 101 could be use to hold the vessel, this will be discussed below. Electrical conduit 115 passes out through the skin of the test animal and directly attaches to a flow-pressure meter 29 (not shown) by a long lead or alternatively attaches to a telemetric pack attached to the outside of the animal and the readings are conveyed by wireless transmission to the flow-pressure sensor meter 29 or computer (not shown). Alternately, electrical conduit 115, may connect to a fully implanted signal telemetry device (not shown) in the subject.

Figure 7:
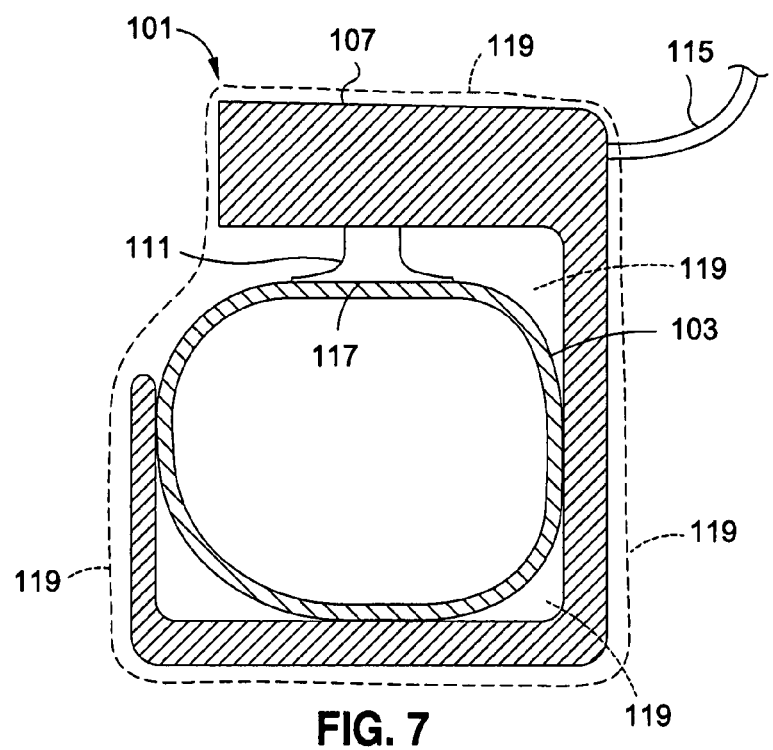
FIG. 7 is a cross sectional cut away view of the probe in FIG. 6 along line VII-VII.

FIG. 7 is a cross sectional cut away view along line VII-VII of FIG. 6. In FIG. 7 a flattened portion 117 of vessel 103 wall can be seen. When a probe, such as probe 101 is chronically implanted, overtime tissue 119 may grow around probe 101 and between probe housing 107 and vessel 103. However, tissue 119 does not negatively affect tonometric sensor 111 because at flattened surface 117 the tissue 119 atrophies and relies on sensing surface 113 for support. This reliance by tissue 119 on the sensing surface 113 enhances the operation of the tonometric sensor 111, as the interposed fibrous tissue 119 becomes passive and thus incapable of altering pressure in vessel 103. Additionally, the tissue growth 119 between housing 107 and vessel 103 forms a uniform transition between ultrasound transceivers 81A and 81B located in housing (not shown in FIG. 7) and vessel 103, which will reduce motion artifacts.

FIG. 8 is another variation of chronically implantable type of probe. In this variation numbering of the various parts disclosed in FIGS. 6 and 7 has been retained. The added feature is an insert or cuff 121. Cuff 121 is made of an acoustically compatible, flexible and reliant material. Cuff 121 is sized to fit into housing 107 of probe 123. As depicted in FIG. 8 cuff 121 has an opening 125 sized conformal to vessel 103, and is designed to fit securely but detachably in housing 107 of probe 123. Cuff 121 is made of a material that is acoustically compatible and biocompatible with vessel 103. Being acoustically compatible with the vessel and blood, the material will not deform the ultrasound fields that derive flow readings from vessel 103. This increases the accuracy of the probe 123. Biological compatibility reduces rejection of the cuff 121 by the body. A material that meets this criteria is Pebax® (Elf-Autchem). A detailed discussion of the insert or cuff 121 appears in Copending provisional application Ser. No. 60/881,826 filed Jan. 23, 2007 and titled "Disposable Insert for a Perivascular Probe Head," which is incorporated herein by reference.

FIG. 9 provides an exploded view of cuff 121 and housing 107 into which cuff 121 is inserted in a secure but detachable fashion. FIG. 10 provides a top view of cuff 121 along line X-X of FIG. 9. As can be seen cuff 121 has a hole 133 in a top of the cuff to receive sensor 111.

Since volume flow and pressure can be measured on the same location of a blood vessel, these measurements make it possible to calculate the impedance of the tissue or organ(s) supplied by the vessel being measured. Impedance Z can be calculated by dividing pressure by flow, the equation would be as follows where P is pressure and Q is flow:

$$Z = \frac{P}{Q} \qquad [4]$$

Values for impedance can be determined with either flow volume, as is the case with the use of transit time ultrasound or with flow velocity as is the case with back scattered Doppler ultrasound system that are discussed below.

One preferred embodiment of the disclosure employs a transit time ultrasound sensor, which fully illuminates the cross sectional area of the vessel 103 with bidirectional beams of ultrasound. It is within the spirit of the disclosure to employ other sensors for the measurement of flow.

Figure 11:
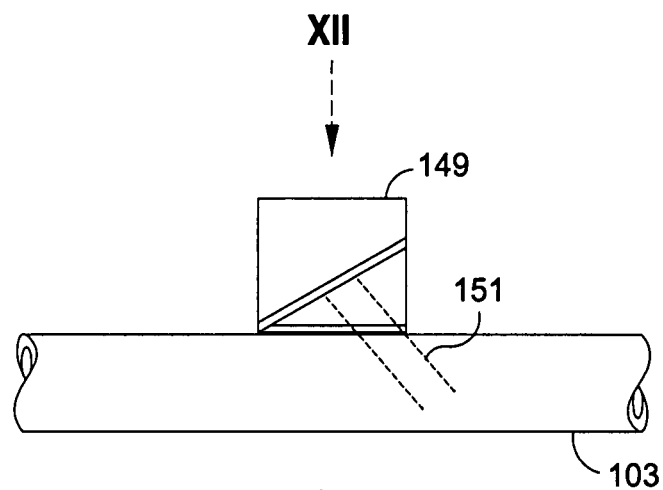
FIG. 11 is a schematic diagram of a Doppler ultrasound system.
Figure 12:
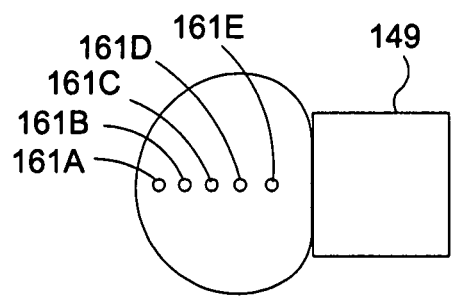
FIG. 12 is a crossectional view of FIG. 11 along line XII.

In another variation, Doppler ultrasound sensors could be used in place of transit time flow sensors. FIG. 11 provides a schematic diagram of a Doppler ultrasound system with the combined tonometric sensor 111 and Doppler sensor 149 adjacent vessel 103. In Doppler ultrasound systems, ultrasound 151 is directed into the vessel 103 at an oblique angle. For a detailed discussion of how a Doppler ultrasound sensor functions, publications and textbooks known by those of ordinary skill in the art adequately sets forth the level of those skilled in the art. In one variation the Doppler ultrasound sensor could be limited to reading flow velocity and not volume flow. However, by taking a series of readings over a cross sectional area of the vessel 103, the internal diameter of the vessel 103 may be determined as well and volume flow may be measured. FIG. 12 provides a cross sectional view of the system of FIG. 11 along line XII, where Doppler ultrasound sensor 149 takes readings of the flow speed at several different cross sectional points 160A, 1608, 160C, 160D and 160E of vessel 103 in order to thereby estimate volume flow.

While the invention has been particularly shown and described with reference to a preferred embodiment thereof, it will be understood by those skilled in the art that various changes in form and detail may be made to it without departing from the spirit and scope of the invention.

The invention claimed is:

1. A method for determining fluid volume flow and a pressure of a fluid flowing along a flattened section of a flexible conduit, the method comprising the steps of:
    making at least two passes of an ultrasound beam emanating from a housing through the flexible conduit at an oblique angle to the fluid flowing in the flexible conduit, wherein the two passes are in opposite directions along a same path, and wherein the ultrasound beam illuminates the fluid flowing in the flexible conduit on each pass;
    determining a change in a characteristic of the ultrasound beam after each pass through the flexible conduit;
    determining the fluid volume flow;
    flattening with a pressure sensor connected to the housing, at a position where the ultrasound wave beam passes through the fluid, a portion of an outside surface of the flexible conduit to form a stationary flat surface without creating a full occlusion in the flexible conduit and;
    obtaining a pressure reading from the outside surface of the flattened portion of the flexible conduit.

2. The method of claim 1 comprising the further step of: calculating an impedance to flow of a portion of the flattened conduit corresponding to the obtained pressure reading and the determined fluid flow volume.

3. The method of claim 1 wherein the conduit is a blood vessel and the fluid is blood.

4. A device for measuring a volume flow and a pressure within a stationary flattened length of a flexible conduit, the device comprising:
- a first ultrasound transducer and a second ultrasound transducer configured to be removably located adjacent to the stationary flattened length of the flexible conduit, the first transducer being positioned upstream of (i) the stationary flattened length and (ii) the second transducer, such that transmission of ultrasound beams between the transducers illuminate and pass through a cross sectional area of the stationary flattened flexible conduit;
- a pressure sensor configured to be removably located adjacent to an outside surface of the flexible conduit along the length of the conduit such that the pressure sensor is configured to shape a surface of the flexible conduit into the stationary flattened surface; and
- a meter operatively connected to the first transducer and the second transducer, and configured to determine the volume flow; and the meter further being operatively connected to the pressure sensor to determine the pressure inside the flexible conduit.

5. The device of claim 4 wherein the flexible conduit is a blood vessel.

6. The device of claim 4 wherein the flexible conduit is a deformable tubing.

7. The device of claim 4 wherein the first transducer and the second transducer are positioned on opposite sides of the flexible conduit.

8. The device of claim 4 wherein the first transducer and the second transducer are positioned on a same side of the flexible conduit and wherein their beams are directed to an ultrasonic reflective surface on an opposite side of the flexible conduit.

9. The device of claim 4 wherein the pressure sensor is one of a strain gauge and a capacitive sensing device.

10. The device of claim 4 wherein the first transducer and the second transducer are configured to transmit ultrasound beams simultaneously.

11. A probe for determining volume flow and pressure of a fluid in a flexible conduit, the probe comprising:
- a.) a frame configured to removably receive a length of the flexible conduit;
- b.) a first transducer mounted to the frame, and configured to transmit a first ultrasound beam along an oblique angle path across the flexible conduit so that the first ultrasound beam illuminates fluid present in the flexible conduit;
- c.) a second transducer mounted to the frame, and configured to receive the first ultrasound beam, and further configured to transmit a second ultrasound beam to the first transducer across the flexible conduit along the oblique angle path;
- d.) a flat tonometric sensing surface having a pressure sensor mounted to the frame, the flat tonometric sensing surface configured to flatten the wall portion of the flexible conduit received within the frame; and
- e.) a meter operably connected to the first transducer, the second transducer and the sensor, and configured to determine the volume flow and the pressure of the fluid in the flexible conduit.

12. A method for determining a flow property and a pressure of a fluid flow passing within a flexible conduit, the method comprising the steps of:
- a) generating from a position adjacent to and outside the flexible conduit at least one ultrasound wave that passes through a cross sectional area of the flexible conduit at an oblique angle to fluid flowing within the flexible conduit;
- b) receiving at least one ultrasound wave after passage through a cross sectional area of the flexible conduit;
- c) determining flow from the received ultrasound wave;
- d) flattening to a fixed position an outside portion of the flexible conduit along a length of the flexible conduit through which at least one ultrasound wave passes by exerting a flat surface of a pressure sensor to the outside portion of the flexible conduit; and
- e) taking a pressure reading from the pressure sensor.

13. The method of claim 12 comprising the further step of determining one additional physical parameter from at least one of the pressure reading and the received at least one ultrasound wave.

14. The method of claim 13 wherein the further step of determining one additional physical parameter is determining an organ impedance in the vicinity of the flexible conduit.

15. The method of claim 13 wherein the further step of determining one additional physical parameter is determining a tissue impedance in the vicinity of the flexible conduit.

16. The method of claim 12 wherein the flexible conduit is a blood vessel.

17. The method of claim 12 wherein the step of generating at least one ultrasound wave comprises generating the at least one ultrasound wave with a transit time ultrasound sensor to illuminate a full cross section of the flexible conduit.

18. The method of claim 12 wherein the step of generating at least one ultrasound wave comprises generating the at least one ultrasound wave with a Doppler ultrasound transducer.

19. A probe assembly for monitoring flow in a conformable conduit, the probe assembly comprising:
- (a) a housing sized to receive a length of the conformable conduit;
- (b) a pressure sensor connected to the housing and having a substantially flat outer surface configuration at a fixed location such that a portion of the length of the conformable conduit locally conforms to the flat outer surface; and
- (c) a first transducer connected to the housing and configured to illuminate a cross section of the conformable conduit with a signal along a signal path, at least a portion of the signal path being within the locally conformed portion of the length of the conformable conduit.

20. The probe assembly of claim 19, wherein the pressure sensor directly contacts an outside surface of the conformable conduit.

21. The probe assembly of claim 19, wherein the housing includes a reflector in the signal path spaced from the first transducer.

22. The probe assembly of claim 19, further comprising a second transducer spaced from the first transducer, wherein the housing includes a reflector in the signal path intermediate to the first transducer and the second transducer.

23. A method of monitoring a flow in a conformable conduit, the method comprising:
- (a) passing an ultrasound signal from a transducer in a probe housing through a length of the conformable conduit; and
- (b) sensing a pressure of a locally conformed region of the conformable conduit along the length of the conformable conduit, the locally conformed region having an outside wall of the conformable conduit being substantially flat and stationary.

24. The method of claim 23, wherein the transducer is an upstream transducer and passing the ultrasound signal includes passing the ultrasound signal through the locally conformed region of the conformable conduit from the upstream transducer to a downstream transducer.

25. The method of claim 23, wherein the transducer is an upstream transducer and further comprising retaining the upstream transducer and a downstream transducer in the probe housing, the ultrasound signal passing from the upstream transducer to the downstream transducer through the conformable conduit.

26. The method of claim 23, wherein the transducer is an upstream transducer and further comprising retaining the upstream transducer, a downstream transducer and a pressure sensor in a probe housing, the ultrasound signal passing from the upstream transducer to the downstream transducer through the conformable conduit, and the pressure sensor intermediate the upstream transducer and the downstream transducer.

* * * * *